(12) United States Patent
Staniforth

(10) Patent No.: US 6,660,303 B2
(45) Date of Patent: Dec. 9, 2003

(54) PHARMACEUTICAL SUPERDISINTEGRANT

(75) Inventor: John Staniforth, Bath (GB)

(73) Assignee: Edward Mendell & Co., Patterson, NY (US)

( * ) Notice: Subject to any disclaimer, the term of this patent is extended or adjusted under 35 U.S.C. 154(b) by 0 days.

(21) Appl. No.: 09/731,238

(22) Filed: Dec. 6, 2000

(65) Prior Publication Data

US 2002/0068084 A1 Jun. 6, 2002

Related U.S. Application Data

(60) Provisional application No. 60/169,174, filed on Dec. 6, 1999.

(51) Int. Cl.$^7$ .............................. A61K 9/14; A61K 9/16; A61K 9/20
(52) U.S. Cl. ........................ 424/489; 424/494; 424/493; 424/464; 424/465
(58) Field of Search ............................... 424/400, 464, 424/468, 489, 494, 488, 486; 514/964

(56) References Cited

U.S. PATENT DOCUMENTS

| | | | |
|---|---|---|---|
| 3,141,875 A | 7/1964 | Battista et al. ............... 260/212 |
| 4,226,848 A | 10/1980 | Nagai et al. .................... 424/19 |
| 4,772,473 A | 9/1988 | Patel et al. .................. 424/457 |
| 4,910,023 A | * 3/1990 | Botzolakis et al. .......... 424/470 |
| 5,108,757 A | 4/1992 | Erdos et al. ................. 424/451 |
| 5,272,191 A | 12/1993 | Ibrahim et al. ................ 524/35 |
| 5,275,824 A | 1/1994 | Carli et al. ................... 424/488 |
| 5,456,921 A | 10/1995 | Mateescu et al. ............ 424/465 |
| 5,468,286 A | * 11/1995 | Wai-Chiu et al. ............ 106/210 |
| 5,585,115 A | 12/1996 | Sherwood et al. ........... 424/489 |
| 5,599,555 A | 2/1997 | El-Nokaly ................... 424/490 |
| 5,725,883 A | 3/1998 | Staniforth et al. ........... 424/489 |
| 5,725,884 A | 3/1998 | Sherwood et al. ........... 424/489 |
| 5,733,578 A | 3/1998 | Hunter et al. ................ 424/489 |
| 5,741,524 A | 4/1998 | Staniforth et al. ........... 424/489 |
| 5,858,412 A | 1/1999 | Staniforth et al. ........... 424/489 |
| 5,866,166 A | 2/1999 | Staniforth et al. ........... 424/489 |
| 5,948,438 A | 9/1999 | Staniforth et al. ........... 424/464 |
| 5,965,166 A | 10/1999 | Hunter et al. ................ 424/489 |
| 5,989,589 A | 11/1999 | Cartilier et al. .............. 424/465 |
| 6,103,219 A | 8/2000 | Sherwood et al. ............. 424/49 |
| 6,106,865 A | 8/2000 | Staniforth et al. ........... 424/489 |

FOREIGN PATENT DOCUMENTS

| | | | |
|---|---|---|---|
| WO | WO9402121 | 2/1994 | ............ A61K/9/22 |
| WO | WO9421236 | 9/1994 | ............ A61K/9/20 |

* cited by examiner

*Primary Examiner*—Michael G. Hartley
*Assistant Examiner*—Sharmila S Gollamudi
(74) *Attorney, Agent, or Firm*—Davidson, Davidson & Kappel, LLC

(57) ABSTRACT

Superdisintegrants which provide improved compressibility compared to prior art superdisintegrants and which does not negatively impact the compressibility of formulations which include high-dose drugs, and methods for obtaining the same are disclosed. The superdisintegrants include a particulate agglomerate of coprocessed starch or cellulose and a sufficient amount of an augmenting agent to increase the compactibility of the superdisintegrant. The augmented superdisintegrant provides a fast disintegration of a solid dosage form when incorporated in sufficient quantity therein, without untowardly affecting the compactibility of the solid dosage form (relative to the solid dosage form without the superdisintegrant).

17 Claims, No Drawings

PHARMACEUTICAL SUPERDISINTEGRANT

This application claims priority from Provisional Application Ser. No. 60/169,174, filed Dec. 6, 1999, the disclosure of which is incorporated herein by reference.

BACKGROUND OF THE INVENTION

The present invention relates to enhanced high functionality excipients in the class of superdisintegrants. Superdisintegrants are typically incorporated into pharmaceutical solid dosage forms (such as tablets including one or more active ingredients) in order to provide improved disintegration of the dosage form. Preferably, other properties, including but not limited to, compressibility, material flow, content uniformity, processing steps, and/or tablet size are maintained or improved.

In order to prepare a solid dosage form containing one or more active ingredients (such as drugs), it is necessary that the material to be compressed into the dosage form possess certain physical characteristics which lend themselves to processing in such a manner. Among other things, the material to be compressed must be free-flowing, must be lubricated, and, importantly, must possess sufficient cohesiveness to ensure that the solid dosage form remains intact after compression.

For example, tablets are formed by pressure being applied to the material to be tableted on a tablet press. A tablet press includes a lower punch which fits into a die from the bottom and a upper punch having a corresponding shape and dimension which enters the die cavity from the top after the tableting material fills the die cavity. A tablet is formed by pressure applied on the lower and upper punches. The ability of the material to flow freely into the die is important in order to ensure that there is a uniform filling of the die and a continuous movement of the material from the source of the material, e.g. a feeder hopper. The lubricity of the material is crucial in the preparation of the solid dosage forms because the compressed material must be readily ejected from the punch faces.

As most drugs have none, or only some, of these properties, methods of tablet formulation have been developed which impart these desirable characteristics to the one or more materials compressed into the solid dosage form. Typically, the material(s) to be compressed into a solid dosage form include one or more excipients which impart the free-flowing, lubrication, and cohesive properties to the drug or drugs being formulated into the dosage form.

Lubricants are typically added to avoid the material(s) being tableted from sticking to the punches. Commonly used lubricants include magnesium stearate and calcium stearate. Such lubricants are commonly included in the final tableted product in amounts of less than 1% by weight.

In addition to lubricants, solid dosage forms often contain diluents. Diluents are frequently added in order to increase the bulk weight of the material to be tableted in order to make the tablet a practical size for compression. This is often necessary where the dose of the drug is relatively small.

Another commonly used class of excipients in solid dosage forms are binders. Binders are agents which impart cohesive qualities to the powdered material(s). Commonly used binders include starch, and sugars such as sucrose, glucose, dextrose, and lactose.

There are three general methods of preparing the materials to be included in the solid dosage form prior to compression: (1) dry granulation; (2) direct compression; and (3) wet granulation. Dry granulation procedures may be utilized when one of the constituents, either the drug or the diluent, has sufficient cohesive properties to be tableted. The method includes mixing the ingredients, slugging the ingredients, dry screening, lubricating and finally compressing the ingredients. In direct compression, the powdered material(s) to be included in the solid dosage form is compressed directly without modifying the physical nature of the material itself. The wet granulation procedure includes mixing the powders to be incorporated into the dosage form in, e.g., a twin shell blender or double-cone blender and thereafter adding solutions of a binding agent to the mixed powders to obtain a granulation. Thereafter, the damp mass is screened, e.g., in a 6- or 8-mesh screen and then dried, e.g., via tray drying, the use of a fluid-bed dryer, spray-dryer, radio-frequency dryer, microwave, vacuum, or infra-red dryer.

A limitation in the use of the direct compression method is that the drug or active ingredient must have the requisite crystalline structure and physical characteristics required for formation of a pharmaceutically acceptable tablet. It is well known in the art, however, that one or more excipients can be included to make the direct compression method applicable to drugs or active ingredients which do not possess the requisite physical properties. For solid dosage forms wherein the drug itself is to be administered in a relatively high dose (e.g., the drug itself comprises a substantial portion of the total tablet weight), it is necessary that the drug(s) itself have sufficient physical characteristics (e.g., cohesiveness) for the ingredients to be directly compressed.

Typically, when making direct compression formulations, excipients which impart good flow and compression characteristics to the material as a whole are added to the formulation which is to be compressed. These desirable properties are commonly imparted to these excipients via a pre-processing step such as wet granulation, slugging, spray drying, spheronization, or crystallization. Useful direct compression excipients include processed forms of cellulose, sugars, and dicalcium phosphate dihydrate, among others. A processed cellulose, microcrystalline cellulose, has been utilized extensively in the pharmaceutical industry as a direct compression vehicle for solid dosage forms. Microcrystalline cellulose is commercially available under the trade name EMCOCEL® from Edward Mendell Co., Inc. and as Avicel® from FMC Corp. When compared to other directly compressible excipients, microcrystalline cellulose is generally considered to exhibit superior compressibility and disintegration properties.

Another limitation in the use of direct compression as a method of tablet manufacture is the size of the tablet. If the amount of active ingredient is high, a pharmaceutical formulator may choose to wet granulate the active ingredient with other excipients to attain an acceptably sized tablet with the desired compact strength. This is because the amount of filler/binder or excipients usually needed in wet granulation is less than that required for direct compression because the process of wet granulation contributes to some extent toward the desired physical properties of a tablet. Thus, despite the advantages of direct compression (such as reduced processing times and costs), wet granulation is widely used in the industry in the preparation of solid dosage forms. Many of those skilled in the art prefer wet granulation as compared to direct compression because this method has a greater probability of overcoming any problems associated with the physical characteristics of the various ingredients in the formulation, thereby providing a material which has the requisite flow and cohesive characteristics necessary to obtain an acceptable solid dosage form.

Due to the popularity of microcrystalline cellulose, pharmaceutical formulators have deemed it desirable to include this excipient in a formulation which is wet granulated prior to tableting. Unfortunately, currently-available microcrystalline cellulose does not hold to the typical principle that the amount of filler/binder needed in wet granulation is less than that in direct compression. It is known that the exposure of the microcrystalline cellulose to moisture in the wet granulation process severely reduces the compressibility of this excipient. The loss of compressibility of microcrystalline cellulose is particularly problematic when the formulation dictates that the final product will be relatively large in the environment of use. For example, if a pharmaceutical formulator desires to prepare a solid oral dosage form of a high dose drug, and the use of the wet granulation technique is deemed necessary, the loss of compressibility of the microcrystalline cellulose dictates that a larger amount of this material may be needed to obtain an acceptably compressed final product. The additional amount of microcrystalline cellulose needed adds cost to the preparation, but more importantly adds bulk, making the product more difficult to swallow. The loss of compressibility of microcrystalline cellulose when exposed to wet granulation has long been considered a problem in the art for which there has been no satisfactory solution. This problem has recently been overcome with the introduction of PROSOLV SMCC™, commercially available from Penwest Pharmaceuticals Co., and described and covered by U.S. Pat. Nos. 5,866,166; 5,725,884; 5,725,883; and 5,585,115, among others. PROSOLV SMCC™ is a silicified microcrystalline cellulose. Silicification of the microcrystalline cellulose is achieved by a patented process, resulting in an intimate association between the colloidal silica and microcrystalline cellulose. This product is available in a median particle size (by sieve analysis) in the region of 50 µm and 90 µm.

Disintegrants are often included in order to ensure that the ultimately prepared compressed solid dosage form has an acceptable disintegration rate in an environment of use (such as the gastrointestinal tract). Typical disintegrants include starch derivatives (including gelatinised starches (e.g., Sta Rx™) or modified starches, e.g. sodium starch glycolate ("SSG")(e.g., Primojel™)), and salts of carboxymethyl cellulose. Some of these disintegrants are called superdisintegrants because of their high efficiency, even at low concentration, and because of their high swelling capacity in the presence of water. It is also known that some materials, such as microcrystalline cellulose (e.g., Avicel PH101.R™ and Avicel PH102.R™, described in U.S. Pat. Nos. 2,978,446; 3,141,875 and 3,023,104) present binding and disintegrating characteristics and therefore are useful both as a binder and a disintegrant. Swelling is one of the decisive factors influencing the disintegrant behavior of compacted pharmaceutical dosage forms and consequently the biopharmaceutical profile of drug substances. Among the various excipients used to promote the disintegration of such dosage forms in its originally primary particles, several substances, classified as swelling disintegrants, are employed.

One commercially available superdisintegrant, Ac-Di-Sol® (which is the acronym of Accelerated Dissolution), (Croscarmellose Sodium) (FMC Corporation) is an internally cross-linked form of sodium carboxymethylcellulose (NaCMC or "SCMC"). Ac-Di-Sol differs from soluble sodium carboxymethylcellulose only in that it has been cross-linked to ensure that the product is essentially water insoluble. It is an odorless, relatively free flowing, white powder. Internal cross-linking is induced by lowering the pH of NaCMC in solution and then heating it, with no chemical additives used. Initially soluble, the cross-linked NaCMC is virtually insoluble, yet still very hydrophillic and therefore swellable. Ac-Di-Sol is said to be effective in both direct compression and wet granulation formulations. The amount of Ac-Di-Sol used in direct compression tableting may vary with typical usage levels between 1 and 3 percent, and the amount of Ac-Di-Sol used in capsule formulations generally ranges from 4–6 percent. Ac-Di-Sol is said to be covered by U.S. Pat. No. 5,272,191. This product is said to be obtained by internally cross-linking sodium carboxymethylcellulose. The cross-linking is said to be achieved thermally without the use of any chemical additive (viz. cross-linking agent) to create a bridge between the macromolecular chains of cellulose. Ac-Di-Sol is said to quickly absorb high amounts of water by swelling, thereby leading to the disintegration of the tablet.

Cross-linked amylose tablets have a low degree of cross-linking swell in aqueous media. International Patent Application No. WO 94/21236 describes powders of cross-linked amylose having a specific cross-linking degree for use as a binder/disintegrant in tablets prepared by direct compression. (See also U.S. Pat. No. 5,456,921 and International Patent Application No. WO 94/02121). Powders of cross-linked amylose with a high cross-linking degree are said to allow tablets to disintegrate quickly by their high capacity of water absorption and their swelling power.

More recently, U.S. Pat. No. 5,989,589 described cross-linked cellulose as a binder disintegrant that can be used in the preparation of pharmaceutical tablets. The binder disintegrant is more specifically said to be a non-swelling cross-linked cellulose having a cross-linking degree ranging from 2 to 50, and is said to be prepared by cross-linking a cellulose (fibrous cellulose or microcrystalline cellulose) with a cross-linking agent (epichlorhydrin, sodium trimetaphosphate, adipic-acetic anhydride, phosphorous oxychloride, formaldehyde and diexpoxides) in a relative amount of 2–50 g of cross-linking agent per 100 g of cellulose.

Another commercially available superdisintegrant, Explotab® and Explotab® CLV (Penwest Pharmaceuticals Co.) is a cross-linked, low-substituted carboxymethyl ether of poly-a-glucopyranose obtained by the suitable treatment of potato starch and has a medium particle size in the range of 35–55 µm. About 50–60 of the glucose units are carboxymethylated. Explotab® CLV differs from standard Explotab® by being more highly cross-linked, resulting in lower viscosity. Explotab® CLV has been demonstrated to be remarkably effective for rapid disintegration and enhanced dissolution when incorporated in tablet formulations prepared by direct compression or wet or dry granulation techniques. The mechanism by which this action takes place involves accelerated absorption of water, leading to an enormous increase in the volume of granules. This results in rapid and uniform tablet disintegration. Explotab® CLV is designed for use in wet granulation processes which utilize modem high-shear, high-speed granulating equipment. It is designed to give the same rapid disintegration as Explotab®, but incorporates qualities which make it more resistant to the rigors of the high-shear granulation process. Explotab® CLV provides desired results at use levels, e.g., between 2–4%. However, it is recommended that the proportion to be included in each individual formulation be determined experimentally.

Each of the above-mentioned U.S. Patents and International Patent Publications are hereby incorporated by reference.

OBJECTS AND SUMMARY OF THE INVENTION

Despite the existence of many binders and disintegrants, there still remains a need in the industry for a pharmaceutical superdisintegrant which is highly compactible and multifunctional (thereby allowing for its use in high-dose formulations, etc.).

It is an object of the present invention to provide an augmented superdisintegrant which has improved compactibility as compared to previously available superdisintegrants.

It is a further object of the invention to provide an augmented superdisintegrant which has improved compactibility as compared to previously available superdisintegrants, while retaining sufficient disintegration properties.

It is a further object of the invention to provide an augmented superdisintegrant which has improved compactibility as compared to previously available superdisintegrants, while retaining disintegration properties which are comparable or better than the state of the art superdisintegrant, i.e., Explotab®.

It is a further object of the invention to provide an augmented superdisintegrant which is multi-functional and which can be used in many formulation circumstances, including possibly providing a lubricant (in cases where the new excipient includes a surface active agent, such as stearic acid).

It is a further object of the invention to provide an augmented superdisintegrant which provides improved compressibility compared to prior art superdisintegrants and which does not negatively impact the compressibility of formulations which include high-dose drugs.

It is a further object of the invention to provide an augmented superdisintegrant which is free-flowing and lubricant-insensitive.

It is a further object of the invention to provide a highly compactible, superdisintegrating drug-ready complex.

It is a further object of the invention to provide a method of obtaining a highly compactible, superdisintegrating drug-ready complex, via the co-transformation of amorphous regions of amylose/amylo-pectin moieties in etherified granules using lubricant-binder emulsion technology.

In accordance with the above objects and others which will be obvious to those skilled in the art, the present invention is directed to a method for improving the compressibility of a superdisintegrant, comprising causing a partial or complete internal co-transformation of the superdisintegrant particles (e.g., using heat or a solvent to temporarily "open-up" the particles and then adding an augmenting agent into the "opened-up" particles which enhances the properties of the superdisintegrant relative to the unmodified particles of the superdisintegrant). Preferably, the augmenting agent enhances the compressibility of the superdisintegrant particles without negatively impacting other desirable properties of the particles, e.g., fast disintegration, etc. Preferably, the superdisintegrant particles may be derived from starch materials or cellulosic materials. Most preferably, the superdisintegrant particles that are modified are selected from sodium carboxymethyl starch cross-linked or sodium carboxymethylcellulose cross-linked.

The invention is also directed to augmented superdisintegrants which are obtained as set forth herein.

In certain embodiments, the invention is further directed to the reduction in elasticity of superdisintegrant particles, by making the core of these particles more hydrophobic.

The invention is further directed to an augmented superdisintegrant, comprising a particulate agglomerate of coprocessed starch or cellulose and a sufficient amount of an augmenting agent to increase the compactibility of said superdisintegrant. The augmented superdisintegrant provides a fast disintegration of a solid dosage form when incorporated in sufficient quantity therein, without untowardly affecting the compactibility of the solid dosage form (relative to the solid dosage form without said superdisintegrant).

By fast disintegration is meant a disintegration time in water at room temperature of less than 2 minutes and preferably less than one minute. Fast dissolution is to be considered as >95% of the drug dissolved in water of 37° C. after 30 minutes. Preferably 90% of the drug has been dissolved after 10 minutes (same conditions).

The relative amount of augmenting agent coprocessed with the starch or cellulose is dependent, in part, upon the type of augmenting agent selected. For purposes of the present invention, the amount is generally described as an effective amount, i.e. an amount which enhances or augments the properties of the superdisintegrant. However, one skilled in the art will appreciate that in certain embodiments of the invention when improved or equal compressibility is not crucial to the preparation of the final solid dosage form, the agglomerated excipient may include an amount of augmenting agent which may not favorably affect disintegration but may instead impart a different beneficial result to the final product, e.g., enhanced compressibility, or even enhanced absorptivity.

In the present invention, it is preferred that the starch-based or cellulose-based superdisintegrant and augmenting agent are in intimate association with each other, such that the augmenting agent is incorporated into the structure of the superdisintegrant particles, in contrast to pharmaceutical formulations which may contain the same ingredients which are merely part of a mixture of ingredients.

The present invention is further directed to a solid dosage form which comprises a therapeutically active agent(s) in admixture with, and preferably compressed together with, an augmented superdisintegrant as described above. In certain preferred embodiments, the solid dosage form is an oral solid dosage form, and the augmented superdisintegrant is incorporated in an amount sufficient to cause the solid dosage form to undergo a fast disintegration as defined above when exposed to aqueous fluids, either in-vitro or in-vivo (e.g., gastrointestinal fluid).

The augmenting agents of the invention may create physical barriers between (at least the outer) layers of the starch granules of starch-based superdisintegrants, or may open up the fibrils of cellulose-based superdisintegrants so that discrete molecular layers no longer exist.

The present invention is further directed to a granulate of an active agent(s) and the novel augmented superdisintegrant excipient described herein. The granulate comprising the augmented superdisintegrant together with a therapeutically active agent(s) and any other optional pharmaceutically acceptable excipients that allow for the production of satisfactory tablets, even with poorly compactible drugs, reduction in tablet size for various high dose drug formulations, and, potentially enhancement of the drug content uniformity of tableted dosage forms, especially in high speed tableting, enhanced disintegration of the final solid dosage form and/or absorptivity of the therapeutically active agent through the lining of the stomach and intestines when the therapeutically active agent is released from the solid dosage form in the gastrointestinal tract.

The invention is also directed to a compressed solid dosage form comprising an active agent(s) and the novel augmented superdisintegrant excipient described herein, wherein the active agent(s) and augmented superdisintegrant excipient have been directly compressed into a solid dosage form or have been subjected to a wet granulation procedure and thereafter compressed into the solid dosage form. The compressed solid dosage form preferably provides an improved compaction of the active ingredient(s) and provides equivalent disintegration of the dosage form in an environment of use. The augmented superdisintegrants of the invention are incorporated into the solid dosage form preferably in an amount from about 0.1 to about 10 percent by weight, more preferably from about 2 to about 5 percent, by weight.

The invention is also directed to a method of obtaining a highly compactible, superdisintegrating drug-ready complex, via the co-transformation of amorphous regions of amylose/amylo-pectin moieties in etherified granules using lubricant-binder emulsion technology. In certain preferred embodiments, the amorphous regions are transformed into crystalline regions.

The invention is also directed to a method of obtaining a highly compactible, superdisintegrating drug-ready complex, comprising preparing a colloidal solution of an augmenting agent selected from the group consisting of a soluble polymer, a surfactant, an oil, and mixtures thereof, and thereafter adding a starch- or cellulose-based superdisintegrant material, to obtain an augmented superdisintegrant cotransformation product. In this aqueous cotransformation, the water may be loaded with a) soluble polymers such as maltodextrin or polyvinylpyrrolidone (PVP); b) surfactants such as poloxamer or sodium laurel sulfate (SLS); c) oils such as stearic acid, glyceryl behenate or magnesium stearate; or d) mixed systems such as stearic acid in aqueous PVP or stearic acid in alcoholic PVP.

The invention is also directed to a method of obtaining a highly compactible, superdisintegrating drug-ready complex, comprising preparing a hot suspension of a starch- or cellulose-based superdisintegrant material (e.g., to a temperature sufficient to "open-up" the particles), and then adding an suitable amount of an augmenting material such as colloidal silica, to obtain an augmented superdisintegrant cotransformation product.

The invention is also directed to a method of obtaining a highly compactible, superdisintegrating drug-ready complex, comprising preparing a hot colloidal solution (e.g., to a temperature sufficient to "open-up" the particles) of a augmenting agent selected from the group consisting of a) soluble polymers such as maltodextrin or polyvinylpyrrolidone (PVP); b) surfactants such as poloxamer or sodium laurel sulfate (SLS); c) oils such as stearic acid, glyceryl behenate or magnesium stearate; or d) mixed systems such as stearic acid in aqueous PVP or stearic acid in alcoholic PVP; and thereafter adding a suitable amount of a starch- or cellulose-based superdisintegrant material, to obtain an augmented superdisintegrant cotransformation product. Preferably, after a stirrable suspension of superdisintegrant material in the colloidal solution is obtained, a suitable amount of a further augmenting material such as colloidal silica is added.

The invention is also directed to a method of obtaining a highly compactible, superdisintegrating drug-ready complex, comprising preparing a solution of an augmenting agent in an aqueous solvent such as aqueous alcohol; and thereafter adding a suitable amount of a starch-based or cellulose-based superdisintegrant material, to obtain an augmented superdisintegrant cotransformation product.

The term "environmental fluid" is meant for purposes of the invention to encompass, e.g., an aqueous solution, or gastrointestinal fluid.

By "bioavailable" it is meant for purposes of the invention that the therapeutically active medicament is absorbed from the solid dosage form which includes the novel agglomerated excipient of the invention, and becomes available in the body at the intended site of drug action.

By "surfactant" it is meant for purposes of the present invention that the material is a surface active agent which displays wetting, detergent or soap-like qualities as those agents are understood by those of ordinary skill in the art.

By temporarily "opening-up" it is meant, for purposes of the present invention, that providing a sufficient degree of cross-linking of the base starch or cellulosic material will allow the grain of starch to expand ("open-up") without rupturing in the presence of heat or a solvent.

The benefits of the novel augmented superdisintegrants of the invention include higher direct compression compactibility (which in turn provides harder, less friable tablets, reduces binder usage/cost, reduces tablet size, and accommodates poorly compactible active ingredients); possibly enhanced material flow (which in turn provides better content uniformity); potentially higher speed tableting; potentially improving the ease of formulation of poorly flowing or high-dose drugs; and preferably preservation of disintegration characteristics of the superdisintegrant.

DETAILED DESCRIPTION OF THE INVENTION

Certain preferred embodiments of the invention are directed to the enhancement of the functionality of cross-linked sodium starch glycolate (aka cross-linked sodium carboxymethylstarch, starch carboxymethyl ether, sodium salt, CAS registry number 9063-38-1) through physical chemical (co-)transformation to cross-linked, substituted starches. In other preferred embodiments, physical chemical (co-)transformation to cross-linked sodium carboxymethyl-cellulose is achieved to obtain similar results.

Chemical substitution (e.g. carboxymethylation) and cross-linking (addition of covalent bonds between hydroxyl groups on the same amylopectin/amylose molecules or between linear segments of different amylopectin or amylose molecules which further reinforce the integrity of the whole starch grain over and above naturally-occurring hydrogen bonds and therefore prevent grain rupture during exposure to heat or a solvent) can be carried out on any native starch. Examples of widely used plant sources for starch include: stable root starches, such as tapioca and potato and waxy starches such as waxy maize (corn). Other sources include wheat, rice (or other cereals) and banana (or other plantain). The preferred commercial form of sodium starch glycolate used in the products Explotab (Penwest Pharmaceuticals Co.) and Primojel (manufactured by Avebe) inter alia use potato starch as the starting material. However, in order to achieve the desired higher functionality it may be desirable to use another form of native starch as the starting material for etherification, cross-linking and co-transformation for reasons explained below.

First, particle size can differ, as different native starches have different particle size and size distributions which probably affect their inherent compactibility. For example, potato starch has the largest grain size ranging down to rice which has the smallest grain size. The significance in grain size/size distribution is in setting a base compactibility. It is assumed that a major reason for selecting potato starch as a base for a superdisintegrant is its large size. However, superior compactibility will likely be conferred by one or a mixture of base options, these being: i) reducing grain size (i.e. selecting another native starch); and ii) altering particle size distribution. The particle size distribution can for example be altered by 1) size selection of sieved potato starch grains; 2) mixing different native starches—some potato/some tapioca/some wheat etc.; or 3) mixing starches from either examples 1 or 2 above with a small mass of fine non-starch excipient (e.g. microcrystalline cellulose, dicalcium phosphate, lactose, colloidal silica).

Those skilled in the art will appreciate that it is considered likely that retention of acceptable superdisintegrant action while improving compactibility will require a trade-off between coarse particles for disintegrant and finer particles or a particle size distribution for compactibility.

Second, the wax content can differ because different native starches have different wax contents. The wax is present as a hydrophobic core which resides down the center of amylopectine/amylose molecular chains. The molecular association is effectively the helical equivalent of the circular association of cyclodextrin molecules around hydrophobic core molecules. It is considered likely that the amount of wax influences both compactibility and disintegrant action. Therefore changing the wax content in one of the following ways as base options seems desirable: i) selection of a different wax content starch starting material—it is considered most desirable to select a low-wax starting material; ii) removing wax from any native starch by solvent washing, which can be carried out, e.g. by using an ethanolic suspension of starch in a rotary evaporator; iii) addition of surfactant materials with different HLB values (Hydrophilic-lipophilic balance) back into either i) or ii) above which can be carried out e.g. by single or repeated washings with the surfactant in solution or suspension followed by drying.

Third, the etherification (the proportion of starch etherified (e.g. sodium carboxymethylated) in the base material) can be changed in order to control properties such as viscosity and pH sensitivity. The pH sensitivity is known to be important as a means of controlling sequestration of particularly amine and carboxylic acid-containing drug molecules on starch surfaces. Low pH starches are therefore favored in cases where anti-adsorption measures for such types of drugs are considered desirable.

Fourth, the degree of cross-linking of the base starch material can be altered as a means of controlling the ease and extent of access of physical chemical co-transforming materials to the starch grain. The range of cross-linking usually goes from 1 cross-link for every 3000 anhydro-glucose units, up to 1 cross-link for every 100 anhydro-glucose units. The significance of the degree of cross-linking is that it effectively sets the resistance of the starch grain to disruption on exposure to heat or a solvent. Effectively, the covalent cross-links reinforce the native hydrogen bonds which weaken and break when a starch grain is heated in the presence of water (causing gelatinization or popcorn) or when exposed to a solvent. This allows the grain to swell significantly without bursting. This property therefore clearly influences the likelihood of molecules or even particles getting into the grain and how deeply and reinforces the structure as a means of improving compactibility following cotransformation. In the base sodium starch glycolate ("SSG"), pre-co-transformation, it is thought that there will be an optimum degree of cross-linking to provide best starting compactibility, based on the effect of cross-linking on material elasticity and visco-elasticity. There could then be a trade-off between such good starting compactibility (which might be favored by low degree of cross-linking) and best compactibility following co-transformation (which might be achieved as a result of a high degree of cross-linking in order to open up the grain without risk of rupture).

The result of optimizing the four factors described above yields a transformed material which may have sufficiently enhanced functionality that becomes a product in its own right. Alternatively (and more likely) it provides an optimum starting material or process conditions for co-transformation.

Co-transformation

The aim of co-transformation is the use of pharmaceutically acceptable additives in (usually) low concentrations to improve the functionality of the main ingredient excipient (in this case sodium starch glycolate or sodium carboxymethylcellulose) as a result of overcoming some weakness in the physical mechanical and/or physical chemical property of the main excipient. Co-transformation yields a product with at least two known excipients which react synergistically, but not chemically, to improve product functionality. Addition of second or higher additives for purposes of co-transformation can be carried out in one of seven places:

a. Prior to etherification and cross-linking
    b. Prior to etherification
    c. Prior to cross-linking
    d. During etherification and cross-linking
    e. During etherification
    f. During cross-linking
    g. Following etherification and cross-linking The most desirable point for co-transformation using different materials is considered likely to differ. For example, it may be that a hydrophilic surfactant could be added beneficially at (a), whereas a particulate additive such as colloidal silica could be added beneficially after (c) and perhaps most beneficially at (g). It could also be that different proportions of the same co-transforming additive or different additives are added at more than one point from a to g.

Augmenting Agents

The list of augmenting agents useful in the augmented superdisintegrants of the invention include those agents disclosed in the augmented microcrystalline cellulose (PROSOLV) formulations described and claimed to date in, for example, U.S. Pat. Nos. 5,866,166; 5,725,884; 5,725,883; and 5,585,115, hereby incorporated by reference, since the superdisintegrant material (e.g., the cellulosic material, cross-linked sodium carboxymethyl cellulose (croscarmellose USP/NF)) will also be subjected to a co-transformation step and co-transformed. For starch, the most beneficial materials can be categorized as follows:

(a) Surface active materials—these materials include hydrophilic oils/waxes such as polyethylene glycols, polyoxyethylenes, poloxamers, sodium lauryl sulphate, docusate sodium etc etc. It also includes hydrophobic oils/waxes such as saturated and unsaturated fatty acids e.g. stearic acid and its salts (including magnesium stearate), glyceryl behenate, sodium stearyl fumarate, beeswax, etc. Materials which have different HLBs depending on hydrophobic chain length, such as sugar esters, may also be used. The surface active materials also include polymers which have surface activity.

(b) Oligomers and Polymers—including but not limited to PVP, maltodextrins, and/or cyclodextrins.

The aim of including (a) or (b) or (a) and (b) above is to interfere with the elastic/viscoelastic nature of the etherified cross-linked starch grain in a manner which reduces this rheology and enhances ductility.

(c) Fillers—this term is used herein in the materials science sense of a particulate additive to a polymer for purposes of strengthening the polymer (e.g. carbon black to rubber or vinyl). In this case, the additive is a fumed or fine particle such as colloidal silica and the polymer is starch. The filler materials include, but are not limited to: i) colloidal silica, titanium dioxide, kaolin, talc (or other silicaceous earth); ii) calcium carbonate, phosphate or other alkaline earth; iii) cellulose, powdered cellulose or microcrystalline cellulose; and/or iv) a sugar (lactose, sucrose, dextrose, dextrates) or sugar alcohol (mannitol, sorbitol, xylitol).

Surfactants which may be used in the present invention as a compressibility augmenting agent generally include all pharmaceutically-acceptable surfactants, with the proviso that the surfactant have an HLB value of at least 10, and preferably at least about 15.

In certain preferred embodiments, the HLB value of the surfactant is from about 15 to 50, and in further embodiments is most preferably from about 15.6 to about 40. Suitable pharmaceutically-acceptable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids range from 12 to 18. Although a large number of alkyl sulfates are available as surfactants, one particularly preferred surfactant is sodium lauryl sulfate, which has an HLB value of about 40.

In the pharmaceutical arts, sodium lauryl sulfate has been used as an emulsifying agent in amounts of up to about 0.1% by weight of the formulation. However, surfactants such as sodium lauryl sulfate have been included in coprocessed microcrystalline cellulose compositions. Moreover, surfactants have been used in the amounts described herein to improve the compressibility of microcrystalline cellulose especially in wet granulations. Sodium lauryl sulfate is a water-soluble salt, produced as a white or cream powder, crystals, or flakes and is used as a wetting agent and detergent. Also known as dodecyl sodium sulfate, sodium lauryl sulfate is actually a mixture of sodium alkyl sulfates consisting chiefly of sodium lauryl sulfate. Sodium lauryl sulfate is also known as sulfuric acid monododecyl ester sodium salt. Furthermore, sodium lauryl sulfate is readily available from commercial sources such as Sigma or Aldrich in both solid form and as a solution. The solubility of sodium lauryl sulfate is about 1 gm per 10 ml/water. The fatty acids of coconut oil, consisting chiefly of lauric acid, are catalytically hydrogenated to form the corresponding alcohols. The alcohols are then esterified with sulfuric acid (sulfated) and the resulting mixture of alkyl bisulfates (alkyl sulfuric acids) is converted into sodium salts by reacting with alkali under controlled conditions of pH.

Alternative anionic surfactants include docusate salts such as the sodium salt thereof. Other suitable anionic surfactants include, without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the invention amphoteric (amphipathic/amphiphilic surfactants), non-ionic surfactants and/or cationic surfactants are included in the coprocessed compositions of the invention. Suitable pharmaceutically-acceptable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone. The HLB for one acceptable non-ionic surfactant, polysorbate 40, is about 15.6.

Other suitable pharmaceutically-acceptable surfactants include acacia, benzalkonium chloride, cholesterol, emulsifying wax, glycerol monostearate, lanolin alcohols, lecithin, poloxamer, polyoxyethylene, and castor oil derivatives.

The augmented superdisintegrant of the invention is preferably free-flowing and directly compressible. Accordingly, the excipient may be mixed in the desired proportion with an active agent and optional lubricant (dry granulation), and then directly compressed into solid dosage forms.

Alternatively, all or part of the augmented superdisintegrant may be subjected to a wet granulation with the active ingredient. A representative wet granulation includes loading the novel excipient particles into a suitable granulator, such as those available from Baker-Perkins, and granulating the particles together with the active ingredient, preferably using an aqueous granulating liquid. The granulating liquid is added to the mixture with stirring until the powdery mass has the consistency of damp snow and then wet screened through a desired mesh screen, for example, having a mesh from about 12 to about 16. The screened granulate is then dried, using standard drying apparatus such as a convection oven before undergoing a final screening. Additional dry screening of this material is possible, such as by using screens of from about 40 to about 200 mesh. Those materials flowing through 40 and 60 mesh screens may be further ground prior to ultimate tablet formulation. The thus obtained granulate containing the novel excipient is now capable of undergoing tableting or otherwise placed into a unit dosage form.

In addition to one or more active ingredients, additional pharmaceutically acceptable excipients (in the case of pharmaceuticals) or other additives known to those skilled in the art (for non-pharmaceutical applications) can be added to the novel excipient prior to preparation of the final product. For example, if desired, any generally accepted soluble or insoluble inert pharmaceutical filler (diluent) material can be included in the final product (e.g., a solid dosage form). Preferably, the inert pharmaceutical filler comprises a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, "off-the-shelf" microcrystalline cellulose, mixtures thereof, and the like.

An effective amount of any generally accepted pharmaceutical lubricant, including the calcium or magnesium soaps may optionally be added to the novel excipient at the time the medicament is added, or in any event prior to compression into a solid dosage form. The lubricant may comprise, for example, magnesium stearate in any amount of about 0.5–3% by weight of the solid dosage form. In embodiments where a surfactant is included as part or all of the compressibility augmenting agent, an additional inclusion lubricant may not be necessary.

The complete mixture, in an amount sufficient to make a uniform batch of tablets, may then be subjected to tableting in a conventional production scale tableting machine at normal compression pressures for that machine, e.g., about 1500–10,000 lbs/sq in. The mixture should not be compressed to such a degree that there is subsequent difficulty in its hydration when exposed to gastric fluid.

The average tablet size for round tablets is preferably about 50 mg to 500 mg and for capsule-shaped tablets about 200 mg to 2000 mg. However, other formulations prepared in accordance with the present invention may be suitably shaped for other uses or locations, such as other body cavities, e.g., periodontal pockets, surgical wounds, vaginally. It is contemplated that for certain uses, e.g., antacid tablets, vaginal tablets and possibly implants, that the tablet will be larger.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), antiepileptics (e.g., phenytoin, meprobamate and nitrazepam), vasodilators (e.g., nifedipine, papaverine, diltiazem and nicardirine), antitussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanol-amine). The above list is not meant to be exclusive.

A wide variety of locally active agents can be used in conjunction with the novel excipient described herein, and include both water soluble and water insoluble agents. The locally active agent(s) which may be included in the controlled release formulation of the present invention is intended to exert its effect in the environment of use, e.g., the oral cavity, although in some instances the active agent may also have systemic activity via absorption into the blood via the surrounding mucosa.

The locally active agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g. acyclovir, idoxuridine, etc.), breath fresheners (e.g. chlorophyll), antitussive agents (e.g., dextromethorphan hydrochloride), anti-cariogenic compounds (e.g., metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-inflammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive. The solid formulations of the invention may also include other locally active agents, such as flavorants and sweeteners. Generally any flavoring or food additive such as those described in *Chemicals Used in Food Processing*, pub 1274 by the National Academy of Sciences, pages 63–258 may be used. Generally, the final product may include from about 0.1% to about 5% by weight flavorant.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857–884, hereby incorporated by reference), stabilizers, binders, odor controlling agents, and preservatives.

Alternatively, the inventive augmented superdisintegrant can be utilized in other applications wherein it is not compressed. For example, the granulate can be admixed with an active ingredient and the mixture then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art and are deemed to be encompassed within the scope of the appended claims.

DETAILED DESCRIPTION OF THE PREFERRED EMBODIMENTS

The following examples illustrate various aspects of the present invention. They are not to be construed to limit the claims in any manner whatsoever.

EXAMPLE 1

Prepare a colloidal solution of stearic acid in polyvinylpyrrolidone (PVP) by adding a hot (90° C.) aqueous solution containing 10% w/w pvp K30 to 2% w/w molten stearic acid, with stirring. Allow the colloidal solution to cool to 70° C. and then add an amount of sodium starch glycolate (e.g. 25% w/w) to produce a stirrable suspension. Stir the sodium starch glycolate suspension for up to 10 minutes, then filter and dry in a convective oven at 70° C. for 8 hours.

EXAMPLE 2

Prepare a colloidal solution of 5% poloxamer in water at 70° C. was produced and then add an amount of ssg to produce a stirrable suspension. Stir the sodium starch glycolate suspension (e.g. 25%) for up to 10 minutes, then filter and dry in a convective oven at 70° C. for 8 hours.

EXAMPLE 3

De-fat and de-water a suspension of 30% w/w ssg in ethanol and de-water using a rotary evaporator. Next, add 2% w/w of sodium lauryl sulphate in water to the ssg to form a stirrable suspension. Stir using a planetary mixer for up to 10 minutes, then filter and dry at 70° C. for 8 hours.

EXAMPLE 4

Prepare a suspension of 30% w/w ssg in water at 90° C. and then add 2% w/w colloidal silica while stirring and continue to stir for 10 minutes. Cool the suspension, filter and dry at 70° C. for 8 hours.

EXAMPLE 5

Prepare a colloidal solution of stearic acid in polyvinylpyrrolidone by adding a hot (90° C.) aqueous solution containing 10% w/w PVP K30 to 2% w/w molten stearic acid, with stirring. Cool the colloidal solution to 70° C. and then add an amount of ssg (e.g. 25% w/w ) to produce a stirrable suspension. Next, add 2% w/w colloidal silica while stirring for 10 minutes. Cool the suspension, filter and dry at 70° C. for 8 hours.

EXAMPLE 6

Prepare a heated suspension of potato starch (30% w/w) in water to 50° C. and containing 2% w/w sodium lauryl sulphate. Gently stir the suspension for 10 minutes. Use the product of this co-transformation as the starting material for etherification and cross-linking.

EXAMPLE 7

Prepare a suspension of sodium starch glycolate in aqueous alcohol containing a 5% PVP. Stir the mixture for 24 hours at room temperature. Filter while washing with a small amount of alcohol, then freeze dry.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A method of obtaining a highly compactible, superdisintegrating drug-ready complex, comprising:

co-transforming amorphous regions of amylose/amylopectin superdisintegrant material in etherified granules using lubricant-binder emulsion technology, said amorphous regions are transformed into crystalline regions, wherein the step of co-transforming using lubricant-binder technology comprises:

a) preparing a hot or heated colloidal solution of an augmenting agent;
    b) adding to said solution said amylose/amylo-pectin superdisintegrant material to form a stirrable suspension at a temperature sufficient to allow said superdisintegrant to swell without bursting;
    c) filtering said stirrable suspension; and
    d) drying said stirrable suspension, to obtain said superdisintegrating drug-ready complex.

2. The method of claim 1, wherein after a stirrable suspension is obtained, a suitable amount of a further augmenting agent is added.

3. The method of claim 1, wherein said augmenting agent is a binder.

4. The method of claim 1, wherein said augmenting agent is a lubricant.

5. The method of claim 1, wherein said augmenting agent is selected from the group consisting of maltodextrin, polyvinylpyrollidine, polaxamer, sodium lauryl sulfate, stearic acid, glyceral behenate, magnesium stearate, and mixtures thereof.

6. A method of obtaining a highly compactible, superdisintegrating drug-ready complex, comprising:

co-transforming amorphous regions of amylose/amylopectin superdisintegrant material in etherified granules using lubricant-binder emulsion technology, said amorphous regions are transformed into crystalline regions, wherein the step of co-transforming using lubricant-binder technology comprises:

a) preparing a hot or heated colloidal solution of an augmenting agent selected from the group consisting of a soluble polymer, a surfactant, an oil, and mixtures thereof;
    b) adding said amylose/amylo-pectin superdisintegrant material to form a stirrable suspension at a temperature sufficient to allow said superdisintegrant to swell without bursting, to obtain an augmented superdisintegrant co-transformation product; and
    c) drying said stirrable suspension, to obtain said superdisintegrating drug-ready complex.

7. The method of claim 6, wherein after a stirrable suspension is obtained, a suitable amount of a further augmenting agent is added.

8. The method of claim 6, wherein said soluble polymer is selected from the group consisting of maltodextrin and polyvinylpyrrolidone.

9. The method of claim 6, wherein said surfactant is selected from the group consisting of polaxamer and sodium lauryl sulfate.

10. The method of claim 6, wherein said oil is selected from the group consisting of stearic acid, glyceryl behenate and magnesium stearate.

11. A method of obtaining a highly compactible, superdisintegrating drug-ready complex, comprising:

co-transforming amorphous regions of amylose/amylopectin superdisintegrant material in etherifled granules using lubricant-binder emulsion technology, said amorphous regions are transformed into crystalline regions, wherein the step of co-transforming using lubricant-binder technology comprises:

a) preparing a hot or heated suspension of said amylose/amylo-pectin superdisintegrant material to a temperature sufficient to allow said superdisintegrant to swell without bursting;
    b) adding a suitable amount of an augmenting agent, to obtain an augmented superdisintegrant co-transformation product; and
    c) drying said stirrable suspension, to obtain said superdisintegrating drug-ready complex.

12. The method of claim 11, wherein after a stirrable suspension is obtained, a suitable amount of a further augmenting agent is added.

13. The method of claim 11, wherein said augmenting agent is a binder.

14. The method of claim 11, wherein said augmenting agent is a lubricant.

15. The method of claim 11, wherein said soluble polymer is selected from the group consisting of maltodextrin and polyvinylpyrrolidone.

16. The method of claim 11, wherein said surfactant is selected from the group consisting of polaxamer and sodium lauryl sulfate.

17. The method of claim 11, wherein said oil is selected from the group consisting of stearic acid, glyceryl behenate and magnesium stearate.

* * * * *